(12) United States Patent
Mikula et al.

(10) Patent No.: US 6,768,115 B2
(45) Date of Patent: Jul. 27, 2004

(54) PROCESS FOR ON-LINE MONITORING OF OXIDATION OR DEGRADATION AND PROCESSABILITY OF OIL SAND ORE

(75) Inventors: Randy Mikula, Edmonton (CA); Brad Bjornson, Fort McMurray (CA)

(73) Assignee: Natural Resources Canada, Ottawa (CA)

( * ) Notice: Subject to any disclaimer, the term of this patent is extended or adjusted under 35 U.S.C. 154(b) by 119 days.

(21) Appl. No.: 10/197,443

(22) Filed: Jul. 18, 2002

(65) Prior Publication Data

US 2003/0015663 A1 Jan. 23, 2003

Related U.S. Application Data

(60) Provisional application No. 60/306,467, filed on Jul. 20, 2001.

(51) Int. Cl.[7] .............................................. G01N 21/35
(52) U.S. Cl. ................................................ 250/339.11
(58) Field of Search ..................................... 250/339.11

(56) References Cited

U.S. PATENT DOCUMENTS

| 4,149,804 | A | | 4/1979 | Chew, III | ................... 356/416 |
|---|---|---|---|---|---|
| 4,236,640 | A | * | 12/1980 | Knight | ........................ 209/587 |
| 4,337,396 | A | | 6/1982 | Lauer et al. | ................. 250/340 |
| 4,433,239 | A | | 2/1984 | Thompson | ................... 250/255 |
| 4,963,745 | A | | 10/1990 | Maggard | .................... 250/343 |
| 5,548,393 | A | * | 8/1996 | Nozawa et al. | ............... 356/70 |
| 2003/0205507 | A1 | * | 11/2003 | Mikula et al. | .............. 208/391 |

* cited by examiner

Primary Examiner—Constantine Hannaher

(57) ABSTRACT

The degree of degradation or oxidation of an oil sand ore feedstock is monitored by near infrared spectroscopy. A beam of near infrared radiation is directed onto the surface of oil sand ore, e.g. on a conveyor belt, to produce reflected radiation and distinctive spectral features are measured indicative of the degree of degradation or oxidation of the oil sand ore. These distinctive spectral features are selected from (a) recording a baseline spectrum shift with decreasing spectral intensity indicating increasing degradation or oxidation, (b) recording spectral peaks in the range 1150 to 1250 nm with said spectral peaks increasing with increasing degradation or oxidation, (c) recording spectral peaks in the range 1700 to 1800 nm with said spectral peaks decreasing with increasing degradation or oxidation and (d) recording spectral peaks in the range 1900 to 2000 nm with said spectral peaks increasing with increasing degradation or oxidation. The recorded spectral values are mathematically converted into signals for controlling operating conditions in an oil sand processing plant.

14 Claims, 6 Drawing Sheets

PROCESS FOR ON-LINE MONITORING OF OXIDATION OR DEGRADATION AND PROCESSABILITY OF OIL SAND ORE

CROSS REFERENCE TO RELATED APPLICATION

This application claims the benefit of U.S. Provisional Application No. 60/306,467 filed Jul. 20, 2001.

BACKGROUND OF THE INVENTION

This invention relates to the use of near infrared (NIR) reflectance spectroscopy for the monitoring of oxidation or weathering (degradation) of oil sand ores.

It is a common practice to commercially extract bitumen from oil sands using the hot water process. In the first step, called conditioning, the oil sand is mixed with water and heated with open steam to form a pulp. Sodium hydroxide or other reagents are added as required to maintain a pH in the range of about 8.0–8.5. After conditioning, the pulp is further diluted so that settling can take place. The bulk of the sand-size particles rapidly settles and is withdrawn as sand tailings. Most of the bitumen floats to the top to form a coherent mass known as bitumen froth which is recovered by skimming.

The oil sand is a quite complex material and includes sand grains, water, clay and bitumen filling the interstices between the sand grains. The concentrations of the components of the oil sands can vary quite widely throughout a deposit and, for instance, Thompson, U.S. Pat. No. 4,433,239 describes the use of near infrared for on-line monitoring of bitumen content in tar sands. For this purpose an infrared reflectance monitor was used with a first filter adapted to pass only wavelengths of about 2180 to about 2260 nm, absorbed by bitumen alone, and a second filter adapted to pass only wavelengths of about 2270 to about 2350 nm, not absorbed by any tar sand components. From a ratio of signals obtained an output is provided which is indicative of the bitumen content. The bitumen readings that were obtained were found to be essentially the same whether or not the tar sand had become dry and oxidized.

It is also known to use near infrared absorbance for measuring the octane of gasoline. This is described in Maggard, U.S. Pat. No. 4,963,745 where the octane number was determined by measuring absorbance in the t-butylmethyene band (1200 to 1236 nm).

It has been found that when oil sand ores become substantially oxidized or degraded, extraction of the bitumen is difficult. For example, a froth may be formed with an elevated mineral to bitumen ratio or there may be a reduced recovery of bitumen. This problem with the processing of oxidized or weathered oil sands is becoming a matter of serious concern as new mines are opened. Many deposits have only a very thin overburden and this results in the upper portion of the oil sand deposit being heavily oxidized, e.g. to a depth of as much as 12 meters. Also because of the activity of underground water, very deep portions of a deposit may also be oxidized. Intermediate portions of the deposits may have little or no oxidation. As such a deposit of oil sand is excavated and fed to a processing plant, e.g. on a conveyer belt, the degree of oxidation of the oil sands may frequently change. These changes have a serious affect on the processing if the processing conditions, amounts of reagents, etc. are not adjusted to compensate for the variations in the degree of degradation or oxidation.

A technique has been developed to quantify the degree of oxidation using microscopic examination of the froth produced. This technique involves creation of a froth sample and characterization of microscopic morphology of the bitumen. Oxidized ore produces a froth with a recognizable bitumen structure different from the unoxidized ore. Quantification of the degree of oxidation is then dependent upon examination of many froth samples and many fields of view to determine the relative amount of oxidation in the original ore. The correlation between the microscopic evaluation of oil sand ore oxidation and processing behaviour has been verified on a batch extraction scale, on a 4 tonne/hour pilot scale and with commercial scale extraction samples.

The above procedure is a complicated way of determining the degree of oxidation and it is an object of the present invention to find a way of on-line monitoring for the degree of oxidation of an oil sand ore and be able to use this information to automatically adjust the processing conditions.

SUMMARY OF THE INVENTION

The present invention in its broadest aspect relates to a unique method of using near infrared (NIR) reflectance for determining the degree of oxidation or degradation of oil sand ores. It has been found according to this invention that the degree of oxidation of an oil sand is not necessarily related to a particular NIR wavelength but can be related to certain aspects of NIR. Thus, it has been found that there are certain NIR wavelengths at which peaks of increasing or decreasing intensity correlate to increasing degrees of degradation or oxidation and that a general downward shift of the spectra baseline may also be correlated to increasing degrees of degradation or oxidation.

By testing a large number of samples using the above microscopic method and obtaining NIR spectra on the same samples, baseline shifts can be obtained indicative of the degree of oxidation of the ore. The degree of degradation or oxidation observed using the above microscopic method strongly correlates with processability of oil sand ores and patterns in the NIR spectra have been found which vary in proportion to the degree of oxidation observed microscopically. For instance, using the spectra baseline shift as the indicator, an ore with no oxidation will provide the highest baseline and an ore that is 100% oxidized will provide the lowest baseline. Using an NIR spectrometer, baseline shifts in NIR spectra can be correlated to the degree of bitumen oxidation or degradation in a wide variety of oil sands.

The baseline shifts can be used in accordance with this invention over a wide range of NIR wavelengths and, for instance, the spectral wavelengths available in commercially available on-line NIR oil sands bitumen measurement devices may be used. These may have spectral values such as 2120 nm, 1936 nm, 1836 nm, 2310 nm, 1723 nm, 2208 nm, etc.

The first region of the NIR spectrum showing a peak intensity relationship to degree of degradation or oxidation is at a wavelength of about 1150 to 1250 nm. In this region, there is a very significant increase in peak intensity with increasing degrees of degradation or oxidation of the oil sand ore.

The second region of the NIR spectrum that can be utilized for measuring the degree of degradation or oxidation is at a wavelength of about 1700 to 1800 nm. Here it has been found that the peak decreases with increasing degrees of degradation or oxidation. This decrease represents a loss of $CH_2$ peak intensity.

The third region of the NIR spectrum that can be related to the degree of degradation or oxidation is found in the region of about 1900 to 2000 nm. Here the peak increases in intensity with increasing degrees of degradation or oxidation and this can be related to an increase in OH intensity.

The spectrometer is typically placed above oil sand to be monitored, e.g. above oil sand moving on a conveyor belt. The instrument continuously produces a measurement which is indicative of the degree of oxidation or degradation of the oil sand ore moving along the conveyor belt into an oil sand processing plant.

Costly chemical additions and/or processor changes, such as chemical additions and times for conditioning, feed rate or water to ore ratio, are necessary to control the processability of oxidized oil sand ores. By continuously monitoring the degree of oxidation and providing a signal indicative the degree of oxidation in accordance with this invention, it is now possible to continuously adjust the processing conditions to an optimum level thereby minimizing production costs.

DESCRIPTION OF THE PREFERRED EMBODIMENTS

EXAMPLE 1

A series of oil sand extractions were carried out using a standard hot water process. The bitumen to mineral ratio (B/M) and bitumen recovery were determined based on different conditioning times for the ore. The B/M ratio is a measure of the froth quality and is determined using an industry standard batch extraction test.

Figure 1A:
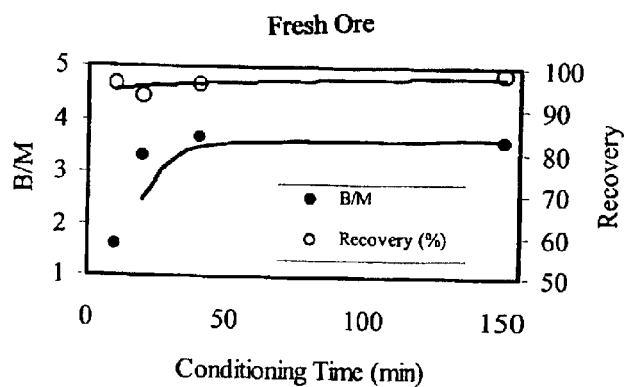
FIG. 1A is plots of B/M and percent bitumen and recovery based on conditioning times for fresh ore.
Figure 1B:
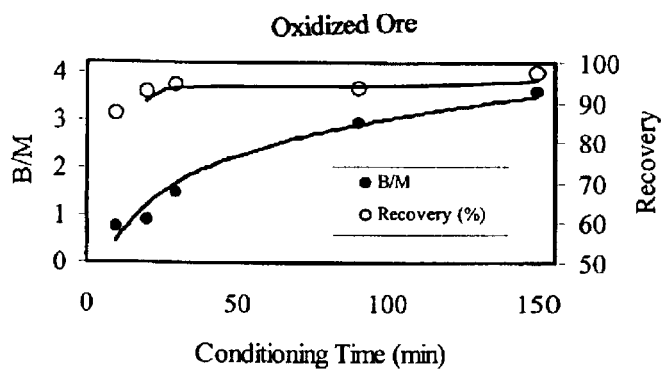
FIG. 1B is plots of B/M and percent bitumen recovery based on conditioning times for oxidized ore.

The results for a fresh (unoxidized) oil sand ore are shown in FIG. 1A, while the results for an oxidized oil sand ore are shown in FIG. 1B. With the fresh ore of FIG. 1A, both recovery and froth quality are high at very short conditioning times. On the other hand, with the oxidized ore of FIG. 1B, more conditioning is required to achieve optimum recovery and even more conditioning is required to optimize froth quality. It has in particular been found that with very poor conditioning, recovery is poor, while at intermediate conditioning levels, recovery is good, but froth quality still suffers.

EXAMPLE 2

The microscopic method described above was used to characterize the degree of bitumen oxidation of a variety of oil sands. From these tests, samples were selected containing (a) less than 5% oxidized ore, (b) 50–60% oxidized ore and (c) >90% oxidized ore. Using an NIR Systems Model 6500 spectrometer, NIR absorbances were measured at a range of wavelengths between 1100 nm and 2500 nm on the two ores. The results are shown in FIG. 2.

Figure 2:
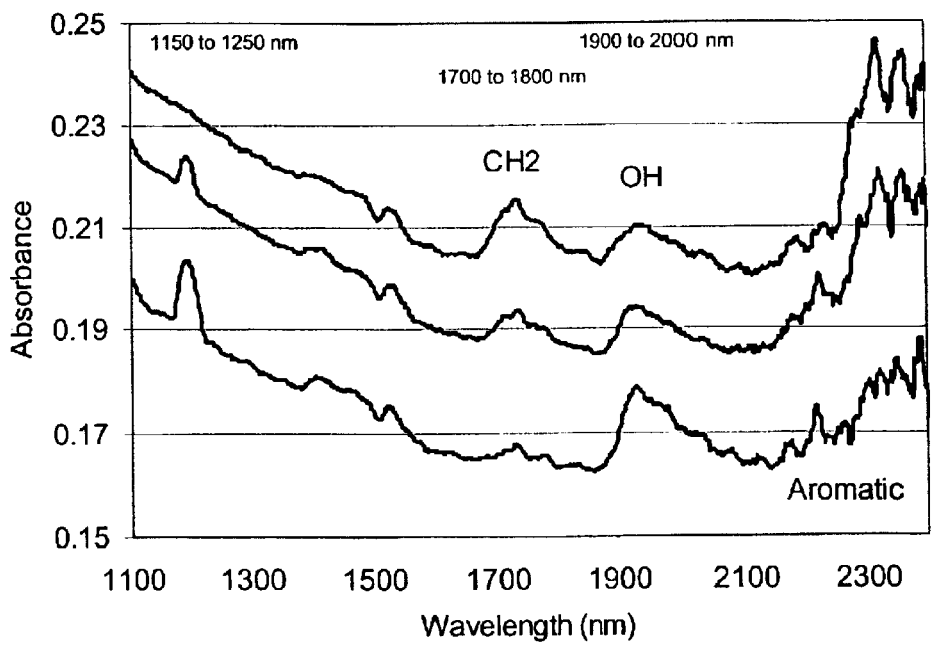
FIG. 2 is a plot of absorbance versus wavelength showing the spectral shift with three oil sands of differing bitumen content.

The spectra of FIG. 2 shows several distinct features which have been found to correlate with the microscopic method for quantifying the degree of degradation, i.e. degradation or oxidation, in an oil sand ore. In FIG. 2, the top line shows an ore that is less than 5% oxidized, the middle line shows an ore that is 50–60% oxidized and the bottom line shows an ore that is greater than 90% oxidized. A significant feature is that the distance between the three spectral lines is approximately constant in substantially all regions where peaks are not occurring. The distance between the spectral lines provide a direct correlation between baseline shift and oil sand oxidation or degradation. It is noteworthy that the spectral shift occurs uniformly across a wide range of frequencies so that, in principle, any frequency that is not coupled to a peak is capable of being used to monitor the spectral shift and thus the degree of oxidation or degradation.

FIG. 2 also shows several noteworthy peaks, the first of these being a peak at a wavelength of about 1200 nm which can be seen to increase with increasing degrees of degradation.

A second significant peak is at a wavelength of about 1750 nm and in this case it can be seem that the peak decreases in intensity with increasing levels of ore degradation. This indicates a decreasing $CH_2$ absorption.

The third peak of significance is at a wavelength of about 1950 nm and in this case the peak intensity increases with increased oxidation or degradation. This indicates an increasing OH absorption.

A further series of peaks may be noted above about 2150 nm and these relate to contents of bitumen, water, solids, etc.

EXAMPLE 3

Figure 3:
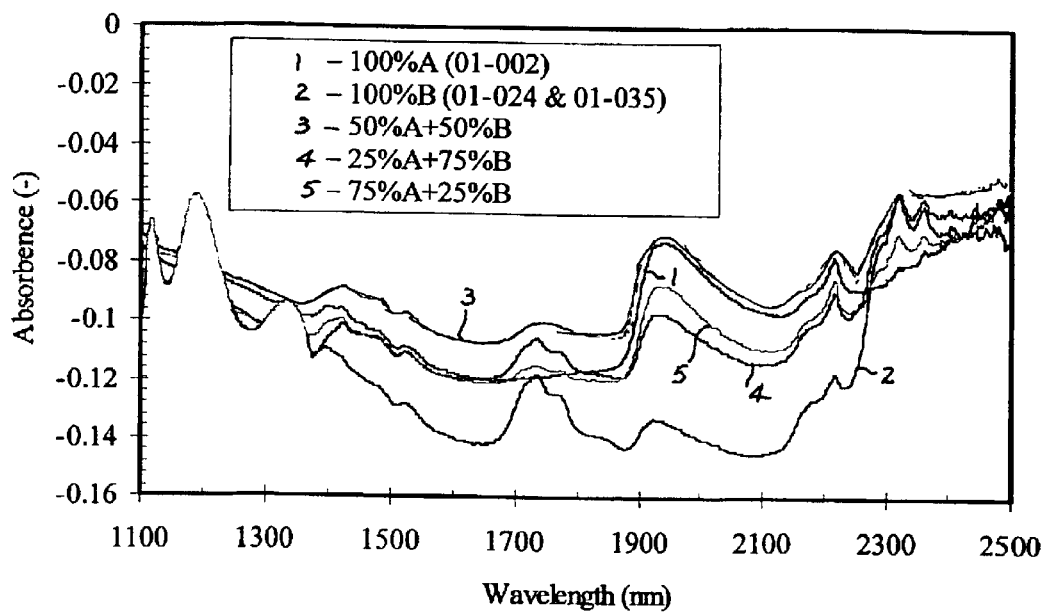
FIG. 3 is a plot of absorbance versus wavelength for a variety of oil sand ores, including those having a high water content.

A series of tests were conducted using (A) oxidized oil sand ore and (B) unoxidized oil sand ore. The ores A and B were tested alone as well as blends of 50%A+50%B, 25%A+75%B and 75%A+25%B. Using the same spectrometer as in Example 2, NIR absorbances were measured at a range of wavelengths between 1100 nm and 2500 nm. The results are shown in FIG. 3.

Due to extreme oxidation, the peak at 1723 nm is reduced. The peaks at 1720 and 1770 nm represent aliphatic carbons and under extreme oxidation these are oxidized from $CH_2$— type groups to C=O and/or C—OH type groups. In this case, the extreme oxidation increases the OH peak intensity at 1900 nm to 1980 nm and this effect washes out the baseline shift that would normally indicate oxidized ore.

However, in this case the degree of oxidation can be correlated directly to the loss of $CH_2$ functional group.

Figure 4:
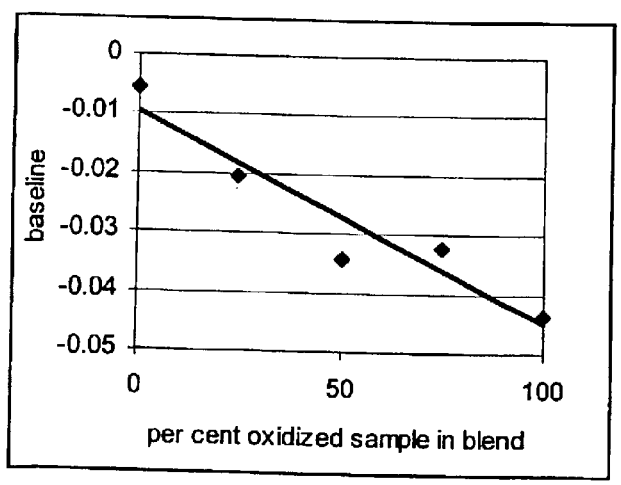
FIG. 4 is a plot of baseline shift versus percent of oxidized ore at 1750 nm.

The correlation in FIG. 4 between baseline and percent oxidation is based on the reduction of the $CH_2$ peak at about 1723 nm. As mentioned above, with extreme oxidation, the baseline peak shift is washed out by a large OH band and in this case a good correlation is developed with the height above baseline of the 1723 nm peak. Thus, the correlation is with the absorbance at 1723 minus the absorbance at 1836 nm. This is a simple measure of the peak height at 1723 nm.

Another ore property that may require separate calibration is the water content of the ore. This is because of the impact of OH as discussed above.

EXAMPLE 4

Figure 5:
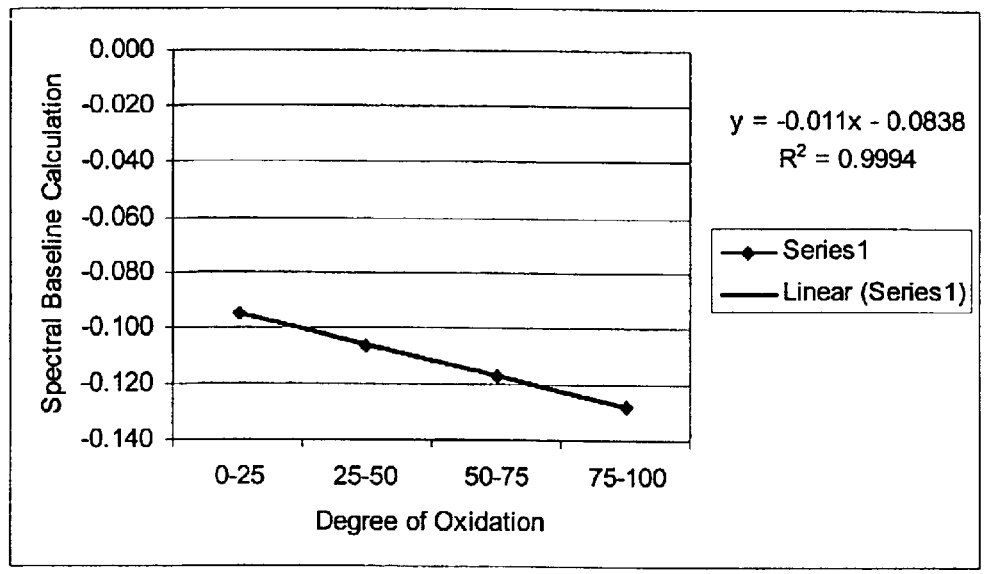
FIG. 5 is a plot of baseline shift versus percent oxidation at a variety of wavelengths.

Further tests were conducted on oil sand ore samples having degrees of oxidation between 0% and 100%. The degree of oxidation for each sample was determined using the microscopic method described above. In FIG. 5, this is shown on the x-axis. The actual data was in 10% increments, but has been combined into only 4 points because of limitations of the operational conditions. In other words, it is unlikely that a commercial scale operation would respond to only 10% changes in the degree of oxidation or processability of the feedstock.

The y-axis is the spectral absorbance at various points in the spectra corresponding to the wavelengths available on the spectrometer that was used, these being 2120 nm, 1936 nm, 1836 nm, 2310 nm, 1724 nm and 2208 nm. The equation used was the peak at 1723 nm minus the peak at 1836 nm minus the peak at 2120 nm. This provided the $R^2$ value of 0.9994.

EXAMPLE 5

Figure 6:
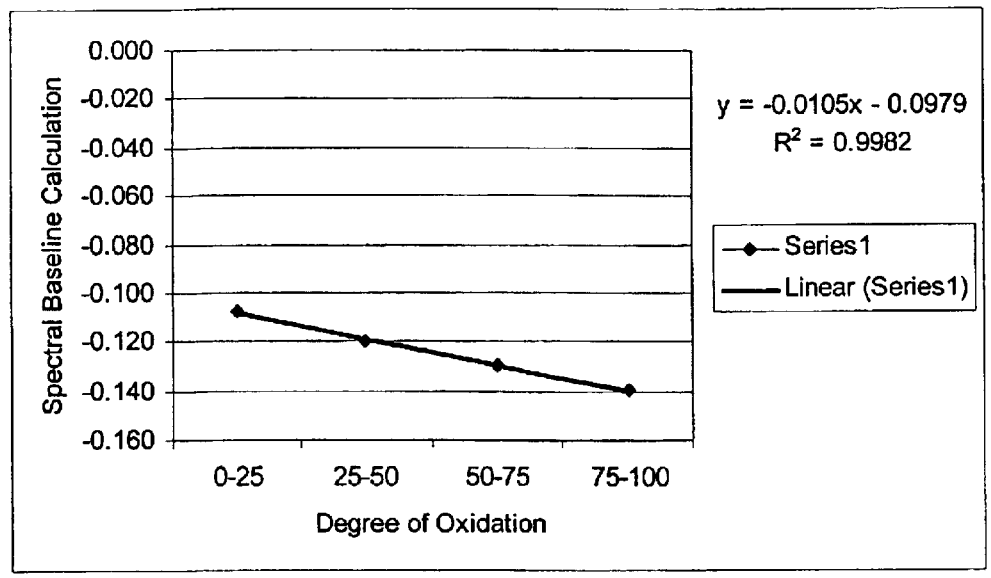
FIG. 6 is a plot of baseline shift versus percent oxidation at 1836 nm.

A correlation between degree of oxidation and spectral baseline calculation was also developed on the basis of spectral values at 1836 nm only. The results are shown in FIG. 6 and even with the one wavelength representing the baseline, a good $R^2$ of 0.9982 was obtained.

These good correlations are due to the general shift in baseline observed in FIG. 2 and show that baseline shift is an excellent way of measuring degree of oxidation by means of a spectrometer. While any points on the spectra are potentially useful as an indicator of oxidation using the method of this invention, it is preferred to avoid wavelengths that are potentially also related to other bitumen properties such as those corresponding to functional groups such as OH (1936 nm) or aromatic groups (2208 nm, 2310 nm). The $CH_2$ group peak (1750 nm) is somewhat different in that it disappears with extreme oxidation. However, in this situation (FIG. 6) the baseline shift is more sensitive and recognizes the oxidation when no changes are observed in the $CH_2$ peak.

EXAMPLE 6

Further tests were conducted to establish a correlation between the NIR spectral response and the degree of oxidation as determined by microscopy. The microscopic observations were binned to include only the average of 0–20% degradation, 20–40% degradation, etc. and the NIR response is based upon the baseline shift.

Figure 7:
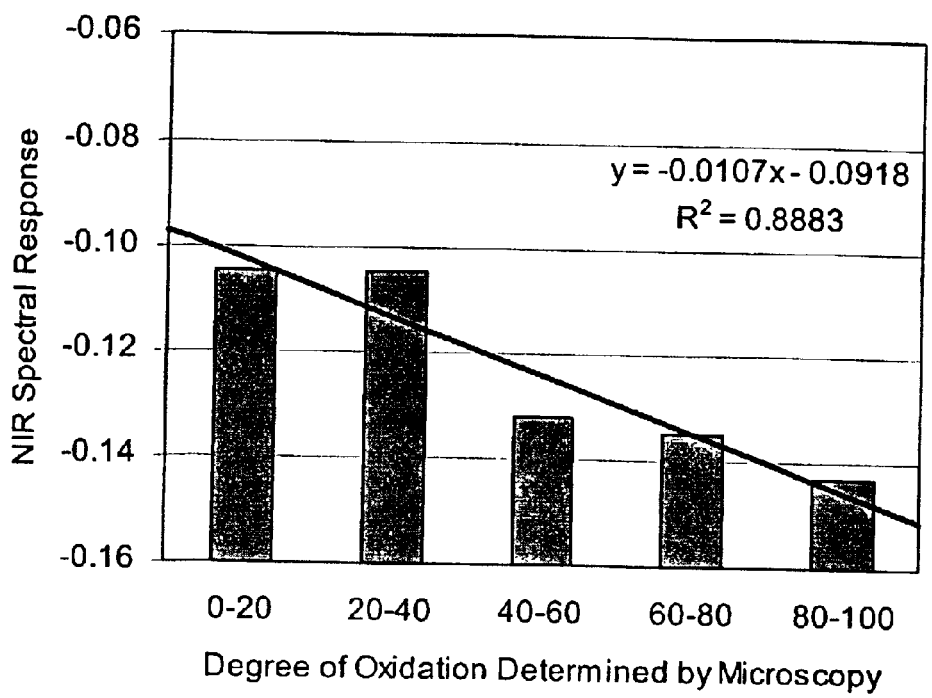
FIG. 7 is a plot of NIR spectral response versus degree of oxidation determined by microscopy.

The results of these tests are shown in FIG. 7 which show a strong correlation between the two techniques.

EXAMPLE 7

Figure 8:
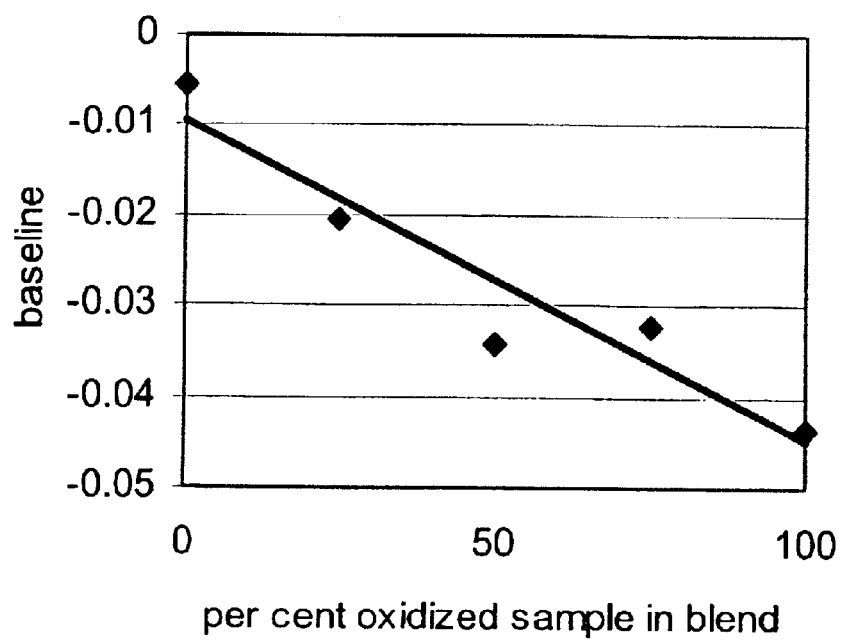
FIG. 8 is a plot of baseline versus percent oxidized sample in blend.

A further study was conducted to determine the correlation of the baseline and 1750 nm peak relative to the percentage of oxidized or degraded ore in the blend. The results shown in FIG. 8 show that a good correlation can be obtained.

EXAMPLE 8

Figure 9:
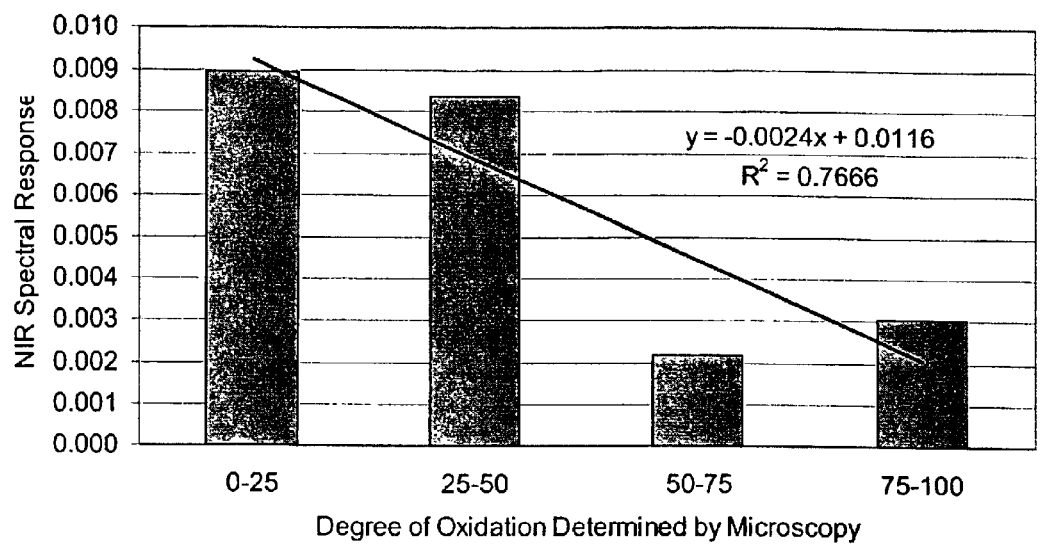
FIG. 9 is a further plot of NIR spectral response versus degree of oxidation determined by microscopy.

The procedure of Example 6 was followed with a different series of samples. Here the microscopic observations were binned to include only the average of 0–25% degradation, 25–50% degradation, etc. As seen from FIG. 9, when the data is averaged and binned, a good relationship emerges between the two methods.

EXAMPLE 9

Figure 10:
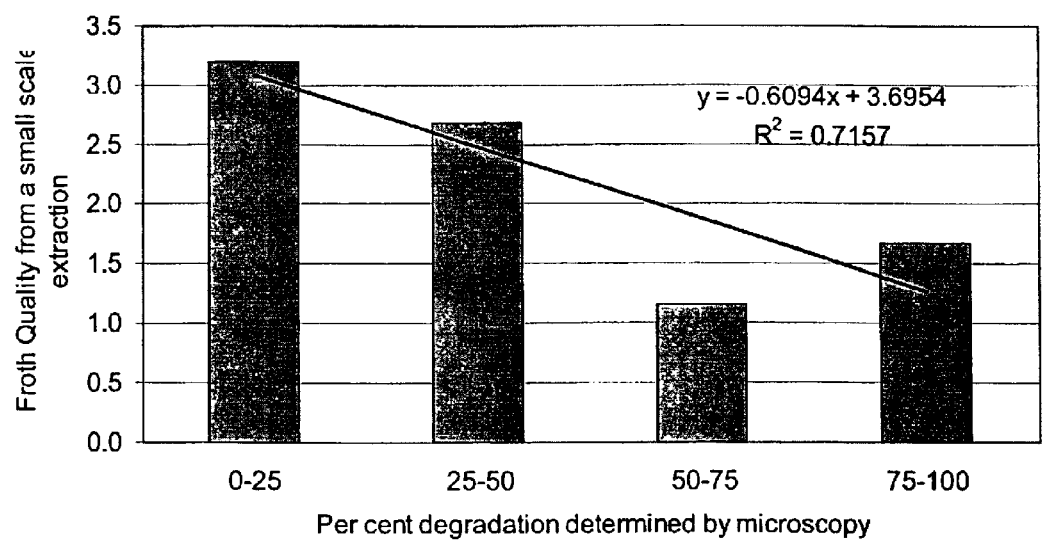
FIG. 10 is a plot of froth quality versus percent degradation determined by microscopy.

Studies were carried out to determine the relationship between the microscopic method and the froth qualities, i.e. a measure of the relative mineral content in the froth. These were based on a series of small scale tests and the results are shown in FIG. 10, which again shows a strong relationship between froth quality and degree of oxidation or degradation of the ore.

EXAMPLE 10

Figure 11:
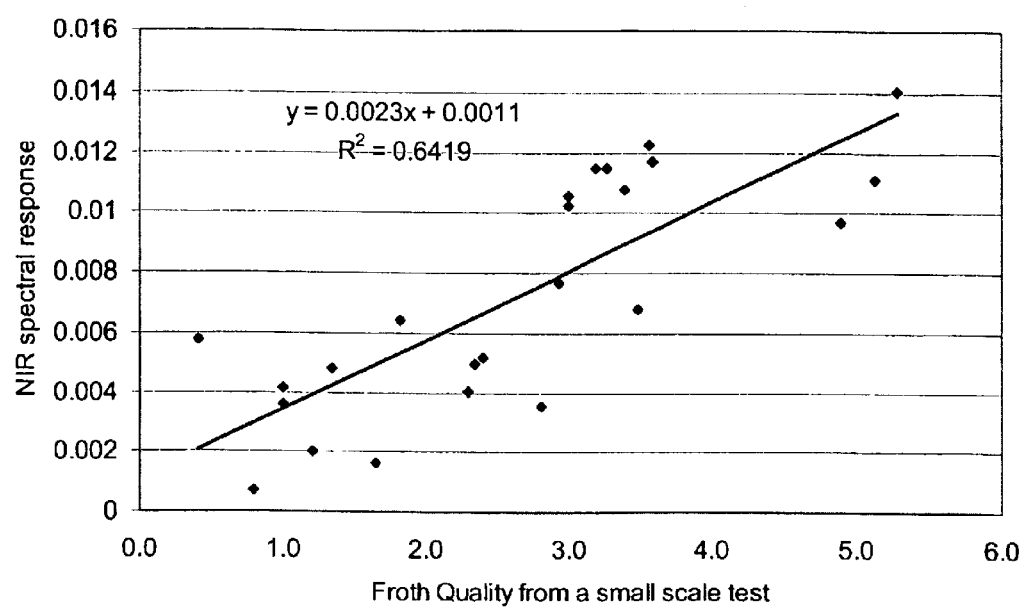
FIG. 11 is a plot of NIR spectral response versus froth quality.

A further plot was carried out to show the relationship between all of the NIR data and all of the froth quality data. The results are shown in FIG. 11 and it indicates a very strong relationship between froth quality and NIR spectral response.

What is claimed is:

1. A method for monitoring the degree of degradation or oxidation of an oil sand ore feedstock by near infrared spectroscopy, which comprises directing a beam of near infrared radiation onto the surface of oil sand ore to produce reflected radiation and measuring distinctive spectral features indicative of the degree of degradation or oxidation of the oil sand ore, said distinctive spectral features being selected from the group consisting of (a) recording a baseline spectrum shift with decreasing spectral intensity indicating increasing degradation or oxidation, (b) recording spectral peaks in the range 1150 to 1250 nm with said spectral peaks increasing with increasing degradation or oxidation, (c) recording spectral peaks in the range 1700 to 1800 nm with said spectral peaks decreasing with increasing degradation or oxidation and (d) recording spectral peaks in the range 1900 to 2000 nm with said spectral peaks increasing with increasing degradation or oxidation.

2. A method according to claim 1 wherein the oil sand feedstock is monitored while travelling on a conveyor belt.

3. A method according to claim 1 wherein the recorded spectral values are mathematically converted into signals for controlling operating conditions in an oil sand processing plant.

4. A method for monitoring the degree of weathering or oxidation of an oil sand ore feedstock by near infrared spectroscopy, which comprises directing a beam of near infrared radiation onto the surface of oil sand ore to produce reflected radiation and measuring the degree of baseline spectrum shift from the baseline spectrum of an oil sand of predetermined degree of degradation or oxidation.

5. A method according to claim 4 wherein the oil sand of predetermined degree of degradation or oxidation is an oil sand ore free of oxidation or weathering.

6. A method according to claim 5 wherein a wavelength is used between about 1100 nm and 2500 nm.

7. A method for monitoring the degree of degradation or oxidation of an oil sand ore feedstock by near infrared spectroscopy, which comprises directing a beam of near infrared radiation onto the surface of oil sand ore to produce reflected radiation and recording spectral peaks in the wavelength range 1150 to 1250 nm with the spectral peak intensity increasing with increasing degradation or oxidation.

8. A method according to claim 7 wherein the peak has a wavelength of about 1200 nm.

9. A method for monitoring the degree of degradation or oxidation of an oil sand ore feedstock by near infrared spectroscopy, which comprises directing a beam of near infrared radiation onto the surface of oil sand ore to produce reflected radiation and recording spectral peaks in the wavelength range 1700 to 1800 nm with the spectral peak intensity decreasing with increasing degradation or oxidation.

10. A method according to claim 9 wherein the decreasing peak intensity represents decreasing $CH_2$ absorption.

11. A method according to claim 10 wherein the peak has a wavelength of about 1750 nm.

12. A method for monitoring the degree of degradation or oxidation of an oil sand ore feedstock by near infrared spectroscopy, which comprises directing a beam of near infrared radiation onto the surface of oil sand ore to produce reflected radiation and recording spectral peaks in the wavelength range 1900 to 2000 nm with the spectral peaks increasing with increasing degradation or oxidation.

13. A method according to claim 12 wherein the peak has a wavelength of about 1950 nm.

14. A method according to claim 12 wherein the increasing peak intensity represents increasing OH absorption.

* * * * *